United States Patent
Berg

[11] Patent Number: 6,033,529
[45] Date of Patent: Mar. 7, 2000

[54] SEPARATION OF MESITYLENE FROM 4-ETHYL TOLUENE BY AZEOTROPIC DISTILLATION

[76] Inventor: Lloyd Berg, 1314 S. 3rd. Ave., Bozeman, Mont. 59715

[21] Appl. No.: 09/369,547

[22] Filed: Aug. 6, 1999

[51] Int. Cl.[7] ................ B01D 3/36; C07C 7/06
[52] U.S. Cl. .............. 203/57; 203/59; 203/60; 585/864; 585/833; 585/860; 585/863; 585/866
[58] Field of Search .................. 203/57, 60, 59; 585/804, 805, 807, 864, 866, 863, 860, 809, 808, 833

[56] References Cited

U.S. PATENT DOCUMENTS

| | | | |
|---|---|---|---|
| 4,168,209 | 9/1979 | Mikitenko et al. | 203/60 |
| 5,401,386 | 3/1995 | Morrison et al. | 208/65 |
| 5,723,026 | 3/1998 | Leisse et al. | 585/807 |

*Primary Examiner*—Virginia Manoharan

[57] ABSTRACT

Mesitylene cannot be separated from 4-ethyl toluene by distillation because of the proximity of their boiling points. They are readily separated by azeotropic distillation. Effective agents are isopropyl palmitate, triacetin and methyl salicylate.

1 Claim, No Drawings

SEPARATION OF MESITYLENE FROM 4-ETHYL TOLUENE BY AZEOTROPIC DISTILLATION

FIELD OF THE INVENTION

This invention relates to a method of separating mesitylene from 4-ethyl toluene using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid said liquid forming an azeotrope with one or more of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off an overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on
Theoretical stage Requirements.

| Separation Purity, Both Products | Relative Volatility Theoretical Stages at Total Reflux | | | | | | | |
|---|---|---|---|---|---|---|---|---|
| (Mole Fraction) | 1.02 | 1.1 | 1.2 | 1.3 | 1.4 | 1.5 | 2.0 | 3.0 |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 28 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce complex mixtures in the mesitylene boiling range. Mesitylene and 4-ethyl toluene boil only one degree apart and have a relative volatilty of 1.05 A process to separate these two would enhance their value as pure compounds. The close relative volatilities make it impossible to separate them by conventional rectification. Azeotropic distillation would be an attractive method of effecting the separation of these two if agents can be found that (1) will create a large apparent relative volatility between mesitylene and 4-ethyl toluene and (2) are easy to recover from mesitylene. Table 2 shows the relative volatility required to obtain 99% purity. With an agent giving a relative volatility of 1.91, only 19 actual plates are required.

TABLE 2

Theoretical and Actual Plates Required vs. Relative
Volatility for Mesitylene - 4-Ethyl Toluene Separation

| Relative Volatility | Theoretical Plates Required At Total Reflux, 99% Purity | Actual Plates Required 75% Efficiency |
|---|---|---|
| 1.37 | 29 | 39 |
| 1.91 | 14 | 19 |

OBJECTIVE OF THE INVENTION

The object of this invention is to provide a process or method of azeotropic distillation that will enhance the relative volatility of mesitylene from 4-ethyl toluene in their separation in a rectification column. It is a further object of this invention to identify organic comounds which in addition to the above constraints, are stable, can be separated from mesitylene and recycled with little decomposition.

SUMMARY OF THE INVENTION

The objects of this invention are provided by a process for separating mesitylene from 4-ethyl toluene which entails the use of certain organic compounds as the agent in azeotropic distillation.

DETAILED DESCRIPTION OF THE INVENTION

I have discovered that certain organic compounds will greatly enhance the relative volatility between mesitylene and 4-ethyl toluene and permit their separation by rectification when employed as the agent in azeotropic distillation. Table 3 lists the compounds that I have found to be effective in separating mesitylene from 4-ethyl toluene by azeotropic distillation. They are isopropyl palmitate, methyl salicylate, 2,6-diethyl aniline, triacetin and ethyl salicylate.

THE USEFULNESS OF THE INVENTION

The usefulness or utility of this invention can be demonstrated by referring to the data presented in Tables 1, 2 and 3. All of the successful agents show that mesitylene can be separated from 4-ethyl toluene by means of azeotropic distillation in a rectification column and the ease of separation as measured by relative volatility is considerable.

TABLE 3

Effective Azeotropic Distillation Agents For
Separating Mesitylene From 4-Ethyl Toluene

| Compounds | Relative Volatility |
|---|---|
| None | 1.05 |
| Isopropyl palmitate | 1.9 |
| Methyl salicylate | 1.32 |
| 2,6-Diethyl aniline | 1.2 |
| Triacetin | 1.51 |
| Ethyl salicylate | 1.2 |

WORKING EXAMPLE

1. Fifty grams of a mesitylene—4-ethyl toluene mixture and fifty grams of isopropyl palmitate were charged to a vapor—liquid equilibrium still and refluxed for two hours. Analysis indicated a vapor composition of 93% mesitylene and 7% 4-ethyl toluene; a liquid composition of 87.5% mesitylene and 12.5% 4-ethyl toluene. This is a relative volatilty of 1.9.

I claim:

1. A method for recovering mesitylene from a mixture of mesitylene and 4-ethyl toluene which comprises distilling a mixture of mesitylene and 4-ethyl toluene in the presence of an azeotrope forming agent, recovering the mesitylene and the azeotrope forming agent as overhead product and obtaining the 4-ethyl toluene as bottoms product, wherein said azeotrope forming agent consists of one material selected from the group consisting of isopropyl palmitate, methyl salicylate, 2,6-diethyl aniline, triacetin and ethyl salicylate.

* * * * *